United States Patent [19]

Balzer et al.

[11] Patent Number: 4,705,649

[45] Date of Patent: Nov. 10, 1987

[54] PREPARATION OF ACYLOXYBENZENESULFONIC ACIDS AND THEIR ALKALI METAL AND ALKALINE EARTH METAL SALTS

[75] Inventors: Wolf-Dieter Balzer, Ludwigshafen; Hans-Heinrich Bechtolsheimer, Dittelsheim-Hessloch; Karl-Heinz Beyer, Frankenthal; Rolf Fikentscher, Ludwigshafen; Johannes Perner, Neustadt; Rudi Widder, Leimen; Helmut Wolf, Hassloch, all of Fed. Rep. of Germany

[73] Assignee: BASF Aktiengesellschaft, Fed. Rep. of Germany

[21] Appl. No.: 928,696

[22] Filed: Nov. 7, 1986

Related U.S. Application Data

[63] Continuation of Ser. No. 731,400, May 7, 1985, abandoned.

[30] Foreign Application Priority Data

May 26, 1984 [DE] Fed. Rep. of Germany ....... 3419793

[51] Int. Cl.$^4$ .................... C07C 69/76; C07C 69/00
[52] U.S. Cl. .................................. 260/402; 560/109; 560/142; 260/513 T; 260/512 R; 260/507 R
[58] Field of Search ........... 260/513 T, 507 R, 512 R, 260/402; 560/109, 142

[56] References Cited

U.S. PATENT DOCUMENTS 3,503,888  3/1970  Miller et al. .................... 252/117
4,321,157  3/1982  Harris et al. .
4,412,934  11/1983  Chung et al. .

FOREIGN PATENT DOCUMENTS 495938   9/1953  Canada ........................... 260/512
864798   3/1958  United Kingdom .
1519351  7/1978  United Kingdom .

OTHER PUBLICATIONS

Gilbert, "Sulfonation & Related Reactions", (1965), pp. 7–18.

Primary Examiner—Alan Siegel
Attorney, Agent, or Firm—Oblon, Fisher, Spivak, McClelland & Maier

[57] ABSTRACT

Acyloxybenzenesulfonic acids and their alkali metal and alkaline earth metal salts are prepared by sulfonation of phenol in the presence of a small amount of a complexing agent for the sulfonating agent $SO_3$ or chlorosulfonic acid, followed by esterification and, if required, neutralization to give the alkali metal or alkaline earth metal salt.

10 Claims, No Drawings

PREPARATION OF ACYLOXYBENZENESULFONIC ACIDS AND THEIR ALKALI METAL AND ALKALINE EARTH METAL SALTS

This application is a continuation, of application Ser. No. 731,400, filed May 7, 1985, now abandoned.

The present invention relates to a process for the preparation of acyloxybenzenesulfonic acids and their alkali metal and alkaline earth metal salts by sulfonation of ohenol in the presence of a small amount of a complexing agent for the sulfonating agent $SO_3$ or chlorosulfonic acid, followed by esterification and, if required, neutralization to give the alkali metal or alkaline earth metal salt.

It is known that acyloxybenzenesulfonic acids, being activated esters, are acylating agents for amines, mercaptans, hydrogen peroxide and other compounds possessing active hydrogen. For some applications, such as the acylation of solids or of water-insoluble polymeric compounds, or for use in detergents as cold bleach activators, for example according to European Patent Application No. 28,432, British Patent No. 864,798, U.S. Pat. No. 4,412,934 or German Published Application DAS No. 2,602,510, water-soluble acylating agents, such as the salts of acyloxybenzenesulfonic acids, e.g. the known benzoyl- or acetyl-p-oxybenzenesulfonates, are advantageous.

The use of salts of acyloxybenzenesulfonic acids in toilet soaps has also been disclosed, for example in U.S. Pat. No. 3,503,888, which describes a procedure for the preparation of acyloxybenzenesulfonic acids, in which phenol is sulfonated with $SO_3$, and the resulting phenolsulfonic acid is esterified with a fatty acid chloride.

Owing to their sensitivity to hydrolysis, it is essential that the acyloxybenzenesulfonic acids are prepared in the absence of water. For this reason, sulfuric acid, which is the usual sulfonating agent for phenol, cannot be employed. The disadvantage of the process described in U.S. Pat. No. 3,503,888 is that the sulfonation does not take place in an optimal manner but with the formation of mixtures of o- and p-isomers and a number of undesirable by-products, such as sulfones and their secondary products, which may have an adverse effect on subsequent working up to give a free-flowing salt since they readily cause caking.

According to the monograph by E. E. Gilbert entitled Sulfonation and Related Reactions, Interscience Publishers, John Wiley & Sons, New York, 1965, chapter 1, for example, $SO_3$ and chlorosulfonic acid form complexes (in general 1:1 adducts) with a large variety of organic compounds, such as amines, pyridine, ethers, amides, etc., and these complexes are milder sulfonating reagents than $SO_3$ or chlorosulfonic acid itself. By means of this complex formation, the reactivity of the sulfonating reagent can be influenced. As a rule, sulfonation with these complexes takes place at higher temperatures than in the absence of a complexing agent and is frequently carried out in the presence of an inert solvent or of an excess of complexing agent. A study of the stated reference shows that the reactivity of such a complex with regard to the substrate being sulfonated cannot directly be predicted.

It is an object of the present invention to provide a process for the preparation of acyloxybenzenesulfonic acids and their alkali metal and alkaline earth metal salts which can readily be carried out on an industrial scale and gives the desired sulfonic acids in high purity and in good yields.

We have found that this object is achieved, and that, surprisingly, the sulfonation of phenol can advantageously be carried out at low temperatures and in the presence of substantially smaller amounts of complexing agents than in the case of a 1:1 complex.

The present invention relates to a process for the preparation of acyloxybenzenesulfonic acids and their alkali metal and alkaline earth metal salts of the formula 1

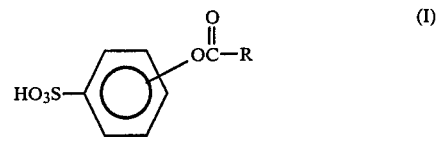

where R is a straight-chain or branched, saturated alkyl radical of 5 to 11 carbon atoms or phenyl, by sulfonation of phenol with $SO_3$ or chlorosulfonic acid followed by esterification, wherein the sulfonation is carried out in the presence of from 0.2 to 20, preferably from 0.6 to 10, mol %, based on the $SO_3$ or the chlorosulfonic acid, of a complexing agent for $SO_3$ or chlorosulfonic acid, at from 20° to 80° C., preferably from 30° to 60° C., and the resulting phenolsulfonic acid is reacted directly with an acyl chloride of the formula Cl-COR, where R has the meanings stated for formula I, at from 25° to 55° C., preferably from 35° to 45° C., and, if desired, the acyloxybenzenesulfonic acid obtained is then neutralized to give the alkali metal or alkaline earth metal salt.

The essential feature of the invention is the addition of a small amount of a complexing agent for $SO_3$ or chlorosulfonic acid, as described in, for example, the stated monograph by Gilbert. The addition of this substance permits the sulfonation to be carried out at a relatively low temperature with good yields and high purity of phenolsulfonic acid. Surprisingly, the conventional 1:1 adducts of $SO_3$ or of chlorosulfonic acid react only very slowly, if at all, in the temperature range according to the invention. Moreover, a larger amount of the complexing agent used, e.g. an amine, entails additional expense inthe working up procedure if a very pure product is desired.

Specific examples of complexing compounds are dioxane, polyalkylene oxides, such as diethylene and dipropylene glycol, whose terminal groups are blocked by alkyl radicals of 1 to 18 carbon atoms, formamide, aliphatic carboxamides of 1 to 10 carbon atoms which are substituted at the amide nitrogen by 1 or 2 alkyl radicals of 1 to 4 carbon atoms, e.g. dimethylformamide, diethylformamide or dibutylformamide, benzamides, 5-membered to 7-membered cyclic amides which are unsubstituted or substituted at the nitrogen by alkyl of 1 to 4 carbon atoms, e.g. N-methylpyrrolid-2-one, N-methylpiperid-2-one or $\epsilon$-caprolactam, triazine derivatives, such as melamine, benzoguanamine or acetoguanamine, trialkylamines where alkyl is of 1 to 6 carbon atoms, N,N-13 $C_1$–$C_4$-dialkylcyclohexylamines, pyridine, triphenylphosphine, amidosulfonic acid, imidazole and boron trifluoride. Mixtures of these complexing agents can, if required, also be used.

Among these, the N,N-disubstituted formamides where alkyl is of 1 to 4 carbon atoms, especially dimethylformamide, and 1,4-dioxane are particularly preferred.

In the novel process, the complexing compound is advantageously added to the molten phenol.

Examples of suitable alkyl radicals R of 5 to 11 carbon atoms are pentyl, heptyl, 2-ethylpentyl, octyl, branched octyl radicals and undecyl.

R is particularly preferably N-heptyl, n-octyl or 3,5,5-trimethylpentyl.

In the preparation, the pure acyl chlorides can advantageously be replaced with the industrially obtainable mixtures which as a rule contain not less than 95% of the defined acyl chloride Cl—COR. In technical terminology, 3,5,5-trimethylhexanoyl chloride is frequently referred to as isononanoyl chloride.

In the reaction mixtures formed, the radical—O—COR in formula I is preferably in the p-position, but a certain amount of the ortho compound is also obtained.

When the phenol to be sulfonated is reacted with $SO_3$ or chlorosulfonic acid, the molar ratio maintained is advantageously about 1:1 so that, for example, sulfone formation, disulfonation and the formation of other byproducts can be avoided. The molar amount of sulfonating agent should advantageously be exceeded by no more than 5 mol %.

The hydrogen chloride formed when chlorosulfonic acid is used can be removed virtually completely and without difficulty in gaseous form, for example under reduced pressure of from 10 to 40 mbar.

The resulting phenolsulfonic acid is advantageously reacted directly with an appropriate acyl chloride at from 30° to 60° C., preferably from 35° to 45° C., in a molar ratio, based on phenol employed. When the reaction is complete, the hydrogen chloride formed is removed as stated above.

The sulfonations described here, including the subsequent esterifications, can be carried out batchwise or continuously. In the continuous embodiment, for example, the reactants can be combined in a tube reactor or in a stirred kettle cascade.

For practical reasons, and because the acyloxybenzenesulfonic acids obtained, being activated phenol esters, are very sensitive to hydrolysis and tend to decompose, it is advantageous to convert the resulting liquid acyloxybenzenesulfonic acids to their alkali metal or alkaline earth metal salts. Among these, the sodium salt is particularly preferred.

In an expedient and particularly advantageous neutralization procedure, the liquid acyloxybenzenesulfonic acid is combined with an aqueous solution of an alkali metal or alkaline earth metal hydroxide, carbonate or bicarbonate in water at from 0° to 60° C., preferably from 10° to 50° C., with thorough mixing, so that the resulting pH is from 2.5 to 7.0, preferably from 3.0 to 5.5, and, if desired, the salt obtained is isolated in solid form in a conventional manner from the aqueous solution.

This special neutralization process, in which acyloxybenzenesulfonic acids can be neutralized without significant hydrolysis, forms the subject of the unpublished German Patent Application No. P 33 37 921.1. The specific procedure is as follows: the liquid acyloxybenzenesulfonic acid and a 5–50% strength by weight aqueous solution of an alkali metal or alkaline earth metal hydroxide, carbonate or bicarbonate are run simultaneously into water at from 0° to 60° C., preferably from 10° to 40° C., while stirring, so that a pH of from 2.5 to 7.0, preferably from 3.0 to 5.5, is maintained.

This neutralization can be effected batchwise or continuously. In the continuous procedure, the components water, acyloxybenzenesulfonic acid and alkali are combined in a static or dynamic mixer.

By means of this neutralization process, it is possible to prepare stable aqueous solutions of the acyloxybenzenesulfonates in concentrations of from 20 to 60% by weight. The pure salts can be isolated from these solutions in a conventional manner, for example by evaporation, drying in a drum drier, spray drying, freeze drying or drying in a fluidized-bed drier.

In a particularly preferred embodiment, this special neutralization procedure is carried out in the presence of from 1 to 2% by weight, based on the acyloxybenzenesulfonic acid, of a water-soluble phosphate, phosphite or tartrate, a complexing agent for heavy metals or a polymer or acrylic acid and/or maleic acid. As a rule the water-soluble sodium salts are used in this procedure.

In this case, the aqueous solutions possess substantially less color and have less tendency to become discolored during further processing when the neutralization is carried out in the presence of these substances. Specific examples are sodium dihydrogen phosphate, disodium tartrate, sodium hydrogen tartrate, sodium phosphite, hypophosphorous acid, nitrilotriacetic acid, ethylenediaminetetraacetic acid, diethylenetriaminepentaacetic acid, hydroxyethylethylenediaminetriacetic acid, nitrilotrimethylenephosphonic acid and polycarboxylic acids obtained from acrylic acid and/or maleic acid and their sodium salts. The polyacrylic acids used have K values of from 15 to 120, and the acrylic acid/maleic acid copolymers possess K values of from 30 to 100, measured in each case as the completely neutralized Na salt in 1% strength by weight aqueous solution at 25° C.

EXAMPLES

The Examples below are carried out using technical-grade 3,5,5-trimethylhexanoyl chloride (isononanoyl chloride). Other acyl radicals behave entirely similarly. The content of acyloxybenzenesulfonic acid in the reaction mixture is advantageously determined after the neutralization with aqueous sodium hydroxide solution and spray drying, on the isolated sodium salts by two-phase titration according to DIN/ISO 2271. Parts are by weight.

1. General method for Examples 1 to 8 and Comparative Examples A and B:

94 parts of phenol were melted, and a complexing agent as shown in Table 1 was added. 122 parts of chlorosulfonic acid or 84 parts of sulfur trioxide were introduced in the course of from 1 to 2 hours at from 45° to 50° C., while cooling. Stirring was continued for 1 hour at 50° C., after which 176.5 parts of 3,5,5-trimethylhexanoyl chloride were added in the course of from 1 to 2 hours at not more than 45° C. After 1 hour, the dissolved hydrogen chloride was virtually completely removed under reduced pressure of from 10 to 20 mbar.

100 parts of the resulting crude acyloxybenzenesulfonic acid were run into 100 parts of thoroughly stirred water. At the same time, 50% strength by weight aqueous sodium hydroxide solution was added dropwise so that the aqueous solution was brought to a pH of from 3.0 to 5.5 (monitored by means of a glass electrode). The temperature of the reaction mixture was kept below 50° C. by cooling. When the addition of the acyloxybenzenesulfonic acid was complete, the solution was brought to pH 5.5, and the sodium salt was isolated from the aqueous solution by spray drying.

EXAMPLE 9

94 parts of phenol were dissolved in 73 parts of dimethylformamide, and the solution was then heated to 40° C. This mixture was sulfonated with 119 parts of chlorosulfonic acid at from 40° to 50° C. in the course of two hours, stirring was continued for 30 minutes at 50° C., and the mixture was then degassed at this temperature under reduced pressure. 176.5 parts of 3,5,5-trimethylhexanoyl chloride were added at from 40° to 50° C. and, after one hour, the dissolved hydrogen chloride was virtually completely removed under reduced pressure of from 10 to 20 mbar and at 50° C.

The crude acyloxybenzenesulfonic acid was neutralized as described above, and the sodium salt was isolated from the aqueous solution by spray drying.

The results are summarized in Table 1. They show that, for a large-scale industrial procedure, the yields have been improved in an unforeseeable manner compared with the comparative experiments.

TABLE 1

|  | ClSO$_3$H | SO$_3$ | Complexing agent | Parts | = Mol %[(2)] | Content of Na salt[(1)] in % |
|---|---|---|---|---|---|---|
| Example |  |  |  |  |  |  |
| 1 | + | − | dimethylformamide | 0.94 | 1.2 | 84.4 |
| 2 | + | − | dimethylformamide | 1.88 | 2.5 | 86.2 |
| 3 | + | − | dimethylformamide | 4.70 | 6.1 | 86.6 |
| 4 | − | + | dimethylformamide | 0.94 | 1.2 | 83.2 |
| 5 | − | + | dimethylformamide | 1.88 | 2.5 | 82.9 |
| 6 | − | + | dioxane | 0.94 | 1.0 | 81.8 |
| 7 | + | − | dioxane | 2.82 | 3.0 | 86.8 |
| 8 | − | + | tetramethylurea | 0.94 | 0.8 | 85.7 |
| Comparative Examples |  |  |  |  |  |  |
| A | + | − | — | — | — | 79.6 |
| B | − | + | — | — | — | 76.1 |
| Example 9 | + | − | dimethylformamide | 73 | 100 | 79.4 |

[(1)]two-phase titration according to DIN/ISO 2271
[(2)]based on ClSO$_3$H or SO$_3$

We claim:

1. A process for the preparation of an acyloxybenzenesulfonic acid or its alkali metal or alkaline earth metal salts of formula (I):

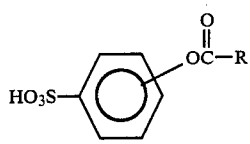

where R is a straight-chained or branched, saturated alkyl radical of 5-11 carbon atoms, or R is phenyl, said process comprising:
  (i) sulfonating phenol with SO$_3$ or chlorosulfonic acid, wherein the sulfonation is carried out in the presence of from 0.2 to 20 mole %, based on the SO$_3$ or the chlorosulfonic acid, of a complexing agent for SO$_3$ or chlorosulfonic acid, at a temperature of from 20°-80° C.;
  (ii) esterifying the resulting phenol sulfonic acid by directly reacting the phenol sulfonic acid with an acyl chloride of the formula Cl-COR at a temperature of from 25°-55° C.; and
  (iii) neutralizing the acyloxybenzenesulfonic acid obtained by combining the liquid acyloxybenzenesulfonic acid obtained with an aqueous solution of an alkali metal or alkaline earth metal hydroxide, carbonate or bicarbonate in water at a temperature of from 0°-60° C., with thorough mixing, and maintenance of the pH to a value from 3.0 to 5.5.

2. A process for the preparation of an acyloxybenzenesulfonic acid or its alkali metal or alkaline earth metal salts of formula (I):

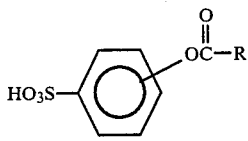

where R is a straight-chained or branched, saturated alkyl radical of 5-11 carbon atoms, or R is phenyl, said process comprising:
  (i) sulfonating phenol with SO$_3$ or chlorosulfonic acid, wherein the sulfonation is carried out in the presence of from 0.6 to 10 mole %, based on the SO$_3$ or the chlorosulfonic acid, of a complexing agent for SO$_3$ or chlorosulfonic acid, at a temperature of from 30°-60° C.;
  (ii) esterifying the resulting phenol sulfonic acid by reacting directly the phenol sulfonic acid obtained with an acyl chloride of the formula Cl-COR at a temperature of from 35°-45° C.; and
  (iii) neutralizing the acyloxybenzenesulfonic acid obtained by combining the liquid acyloxybenzenesulfonic acid obtained with an aqueous solution of an alkali metal or alkaline earth metal hydroxide, carbonate or bicarbonate in water at a temperature of from 0°-60° C., with thorough mixing, and maintenance of pH at a value of from 3.0 to 5.5.

3. The process of claim 1, comprising using as the said complexing agent a N,N-di-(C$_{1-4}$-alkyl) substituted formamide, dioxane, or N-methyl-2-pyrrolidone.

4. The process of claim 2, comprising using as the said complexing agent a N,N-di-(C$_{1-4}$-alkyl) substituted formamide, dioxane, or N-methyl-2-pyrrolidone.

5. The process of claim 1, comprising carrying out the neutralization at a temperature of from 10°-40° C.

6. The process of claim 2, comprising carrying out the neutralization at a temperature of from 10°-40° C.

7. The process of claim 1, comprising carrying out the neutralization in the presence of from 1-2% by weight, based on the acyloxybenzenesulfonic acid, of a soluble phosphate, phosphite or tartrate, a complexing agent for heavy metal salts, a polymer of acrylic acid, a polymer of maleic acid, or a copolymer of acrylic acid and maleic acid.

8. The process of claim 2, comprising carrying out the neutralization in the presence of from 1–2% by weight, based on the acyloxybenzenesulfonic acid, of a soluble phosphate, phosphite or tartrate, a complexing agent for heavy metal salts, a polymer of acrylic acid, a polymer of maleic acid, or a copolymer of acrylic acid and maleic acid.

9. The process of claim 1, comprising using as the complexing agent N-methyl-2-pyrrolidone.

10. The process of claim 2, comprising using as the said complexing agent N-methyl-2-pyrrolidone.

* * * * *